United States Patent [19]

Spalding et al.

[11] Patent Number: 5,776,203

[45] Date of Patent: Jul. 7, 1998

[54] METATARSAL PHALANGEAL SESAMOID PROSTHETIC JOINT

[76] Inventors: Robert Tucker Spalding, 6673 Cherry Bark Dr., Memphis, Tenn. 38141; Kenneth Dernell Mitchell, 315 89th Apt 1FW, New York, N.Y. 10128; Chris Dipersio, #6 Brookdale Rd., Glencove, N.Y. 11542

[21] Appl. No.: 782,747

[22] Filed: Jan. 13, 1997

[51] Int. Cl.⁶ .................................................. A61F 2/42
[52] U.S. Cl. ...................................................... 623/21
[58] Field of Search .............................. 623/16, 18, 20, 623/21

[56] References Cited

U.S. PATENT DOCUMENTS

| | | | |
|---|---|---|---|
| 3,651,521 | 3/1972 | Devas | 623/21 |
| 4,156,296 | 5/1979 | Johnson et al. | 623/21 |
| 4,242,759 | 1/1981 | White | 623/21 |
| 4,685,919 | 8/1987 | Niwa et al. | 623/21 |
| 5,037,440 | 8/1991 | Koening | 623/21 |
| 5,147,386 | 9/1992 | Carignan et al. | 623/21 |
| 5,314,486 | 5/1994 | Zang et al. | 623/21 |
| 5,458,648 | 10/1995 | Berman et al. | 623/21 |
| 5,507,821 | 4/1996 | Sennwald et al. | 623/21 |

FOREIGN PATENT DOCUMENTS

| | | | |
|---|---|---|---|
| 572339 | 12/1993 | European Pat. Off. | 623/21 |
| 2697155 | 4/1994 | France | 623/21 |
| 2126097 | 3/1984 | United Kingdom | 623/21 |

*Primary Examiner*—Mary Beth Jones
*Attorney, Agent, or Firm*—Alan Ruderman

[57] ABSTRACT

A prosthetic or artificial joint for replacing the natural metatarsal-phalangeal-sesamoid joint of the human toe has a phalangeal component that provides an articulating base platform for a metatarsal component to glide upon. The metatarsal component articulates against a gliding articular insert recessed in the base of the phalangeal component. The base of the phalangeal component has an elongated groove which divides the base into two portions which simulate the function of the sesamoids and offers mechanical advantage to the metatarsal component as it articulates. The groove also allows the flexor halucis brevis tendon to pass beneath the joint between the two artificial sesamoids.

2 Claims, 5 Drawing Sheets

METATARSAL PHALANGEAL SESAMOID PROSTHETIC JOINT

BACKGROUND OF THE INVENTION

This invention relates to a prosthetic joint for replacing the metatarsal-phalangeal joint of a human toe, and more particularly to such a prosthesis having a phalangeal component which simulates the function of the sesamoid bones and includes an elongated groove permitting passage of the flexor halucis brevis tendon.

Several protheses have been developed for replacement of the first metatarsophalangeal joint to treat pathological conditions of this joint. Many of these implant designs include elastomeric polymeric materials, alloy metals and/or combinations thereof. The basic design of these models appear as a ball and socket design with opposing concave and convex surfaces articulating exceptionally without mechanical advantages. Examples of the design are Koenig and Frish, U.S. Pat. Nos. 5,037,440 and 4,908,031 respectively. The metatarsal components of Koenig and Frish articulates freely with the pharlangeal components without accounting for sesamoid bones which generally are removed surgically along with the joint.

All other joint implants to this date fail to accommodate or provide a functional replacement for the two plantar sesamoidal bones that articulate with the plantar condyles of the first metatarsal. Moreover, not only does the prior art not appear to provide for replacement of these bones which help reduce mechanical friction while walking or running and help the joint avoid direct contact with the ground, but the prior art does not appear to account for the tendon of the flexor halucis.

SUMMARY OF THE INVENTION

Consequently, it is a primary object of the present invention to provide a metatarsal-phalangeal joint prosthesis which provides mechanical advantage for the metatarsal by keeping sesamoidal support beneath the joint.

It is another object of the present invention to provide a metatarsal-phalangeal joint prosthesis which includes a sesamoidal replacement component with a groove for permitting passage of the flexor halucis tendon.

The prosthetic joint of the present invention is helpful for a number of conditions such as: arthritis, gout, hallux ridgitus, hallux limitus, trauma, degenerative joint disease, septic joints, hallux abducto valgus surgery and sesamoidal fracture. Additionally, the joint of the present invention significantly increases mechanical advantage by keeping an artificial sesamoids portion of the phalangeal component of the prosthesis under the implant and increases leverage upon weight bearing or closed kinetic chain range of motion. This accounts for the replacement of articulation of the natural sesamoids with the plantar aspect of the metatarsal head condyles. The invention provides two basic moving parts that are further guided into bone by two titanium coated stems. This coating helps for osseous integration of the implant stem within the phalangeal base and the metatarsal neck. The joint implant body is formed three subassemblies for manufacturing purposes. A titanium coated metatarsal stem inserts the metatarsal of the remaining surgical distal neck of the first metatarsal. A titanium coated phalangeal stem is attached to a cobalt/chromium alloy artificial dual sesamoid support which articulates proximally with a cobalt/chromium alloy metatarsal implant head and inserts distally into the base of the proximal hallux. A gliding articular insert also attaches anteriorly to the connected artificial dual sesamoid support. The flexor longus tendon travels plantarly inside the plantar artificial condylar channel or flex groove of the artificial dual sesamoids support. This tendon may be teniodesed to the proximal aspect of the proximal phalanx of the hallux to increase hallux purchase. The extensor hallucis longus tendon may travel on the dorsal aspect of the prosthetic joint.

The artificial dual sesamoid support on the plantar surface of phalangeal component is curved at its outermost surfaces for minimization of friction on tissue. The lesser metatarsal phalangeal joints can also utilize this joint design.

BRIEF DESCRIPTION OF THE DRAWINGS

The particular features and advantages of the invention as well as other objects will become apparent from the following description taken in connection with the accompanying drawings in which.

DESCRIPTION OF THE PREFERRED EMBODIMENT

Figure 1:
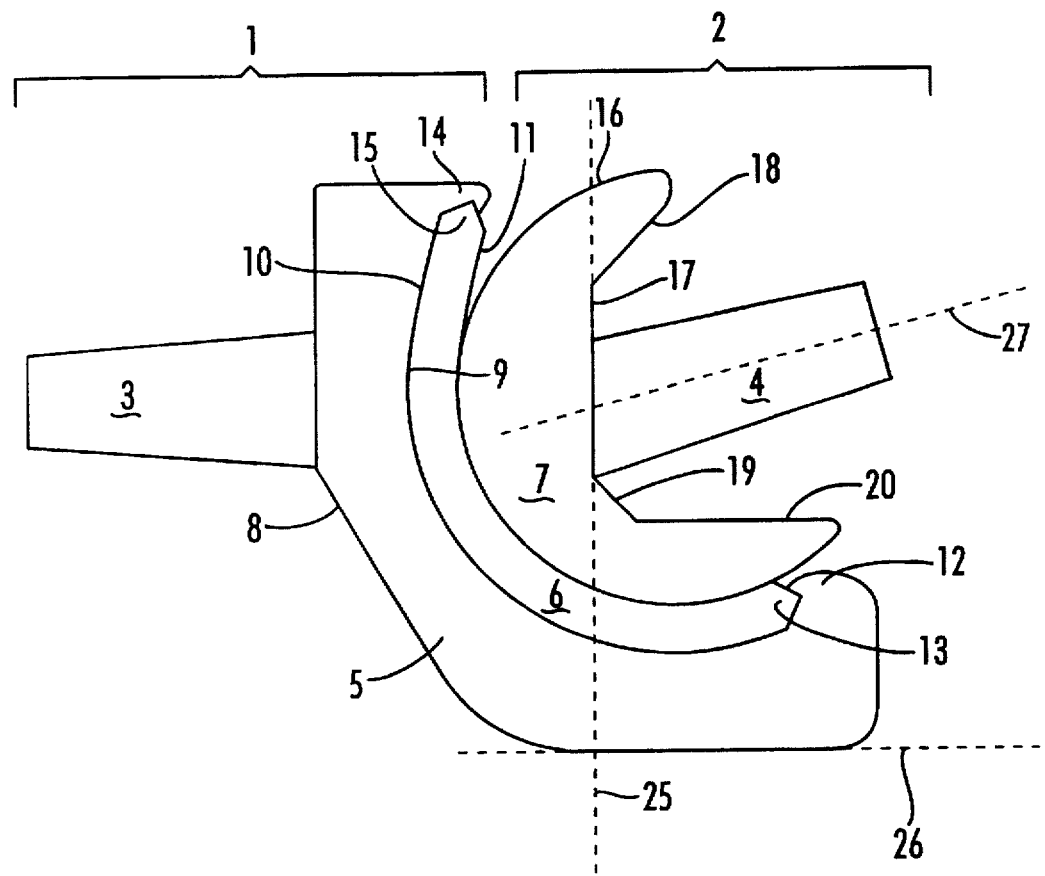
FIG. 1 is an elevational view of a prosthetic joint constructed in accordance with the present invention.
Figure 3:
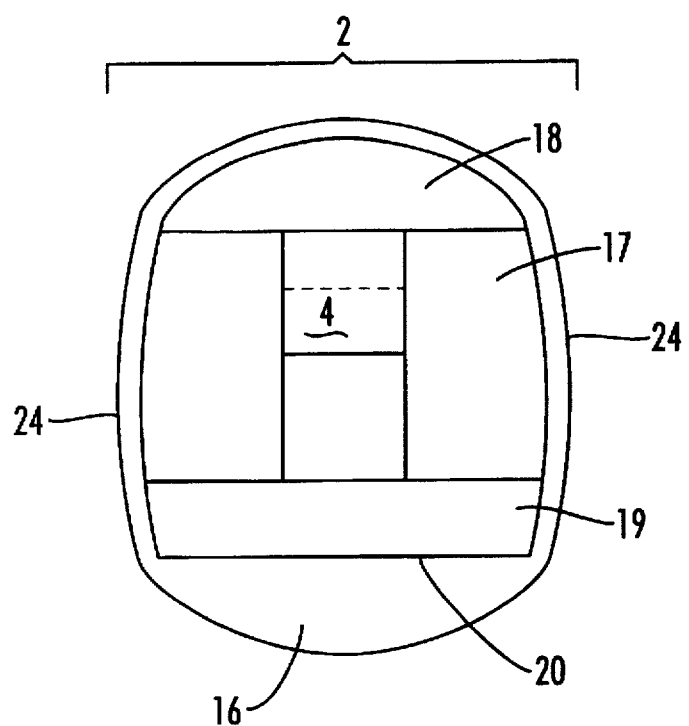
FIG. 3 is a front elevational view of the metatarsal component of the joint as viewed from the posterior of the joint.

Referring to the drawings, and in particular to FIG. 1, a prosthetic joint constructed in accordance with the present invention includes a phalangeal component 1 having a configuration for articulating with a metatarsal component 2, both components being formed from a cobalt/chromium alloy. The phalangeal component 1 comprises an artificial dual sesamoid support member 5, hereinafter merely designated as the dual sesamoid support, including a base portion and a rear or anterior facing stem 3, the stem extending form a convex rear or anterior toe facing surface 8 of the dual sesamoid support 5. The metatarsal component 2 comprises an implant head 7 facing the phalangeal component and includes a forward or posterior facing stem 4 extending from a posterior surface 17 of the metatarsal head 7. As illustrated in FIG. 3, the outer surfaces 24 of the metatarsal head 7 are convex as is the anterior articulating surface 16 which faces the phalangeal component and acts as a bearing surface. The stems 3 and 4 of both the phalangeal component and the metatarsal component are titanium coated, as is known in the art.

Figure 2:
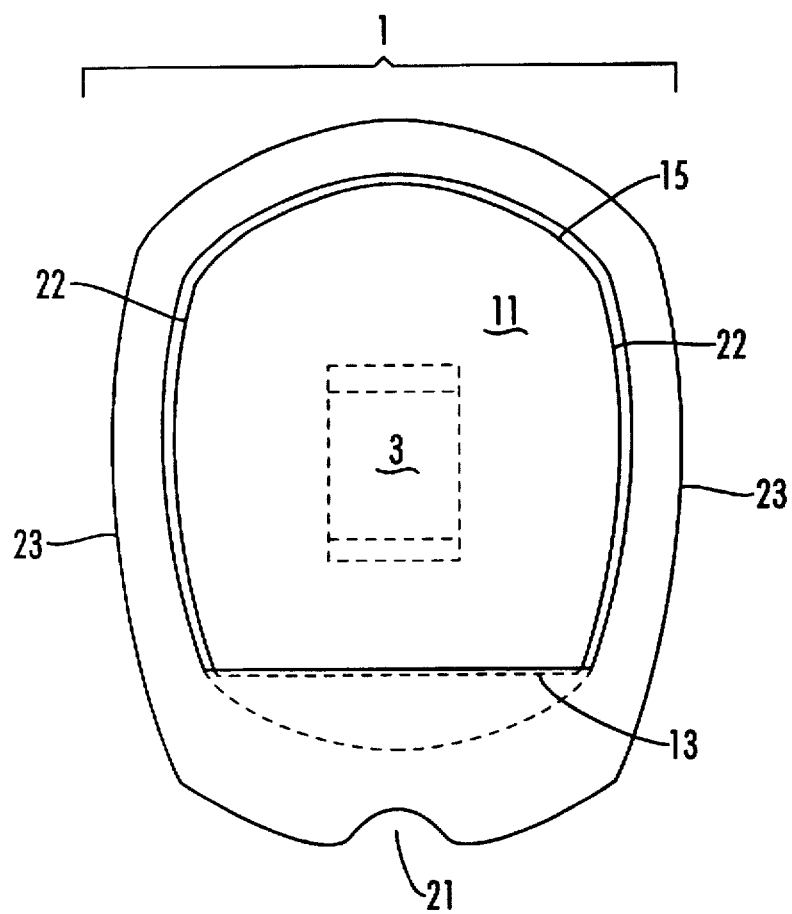
FIG. 2 is a front elevational view of the phalangeal component of the joint as viewed from the posterior of the joint.

The dual sesamoid support 5 is convexly curved at the anterior surface 8, additionally the base of the sesamoid support 8 curves up under the metatarsal head as illustrated in FIG. 1 and thereby maintains a continuous placement beneath the metatarsal head throughout the gate cycle of the person in whom the prosthesis is implanted. This permits the metatarsal to improve the pivoting mechanical advantage of the articulating surfaces. The dual sesamoid support 5, as illustrated in the drawings, has a forward facing or posterior concave shaped surface 9 against which an anterior convex surface 10 of a gliding articular insert 6 is firmly pressed, the gliding articulate insert 6 being formed form a high density molecular weight plastic polymer material. The insert 6 aids the dual sesamoid support member 5 in supporting the metatarsal head 7. The anterior convex surface 16 of the metatarsal head 8 directly contacts the posterior concave bearing surface 11 of the gliding articular insert 6 to minimize friction. Thus, the joint of the present invention provides a normal smooth gliding articular surface between the metatarsal implant head 7 and the phalangeal component. The dual sesamoid support member 5 at the concave posterior face is recessed and terminates at the inferior or lower edge and the superior or upper edge in recess retaining notches 12, 14, respectively. The notches 12, 14 respectively receive a posterior inferior edge 13 and an anterior superior edges 15 of the gliding articular insert 6. As illustrated in FIG. 2, the outer edge 22 of the gliding articular insert is received within the outer convex surface 23 of the dual sesamoid support 5.

Figure 5:
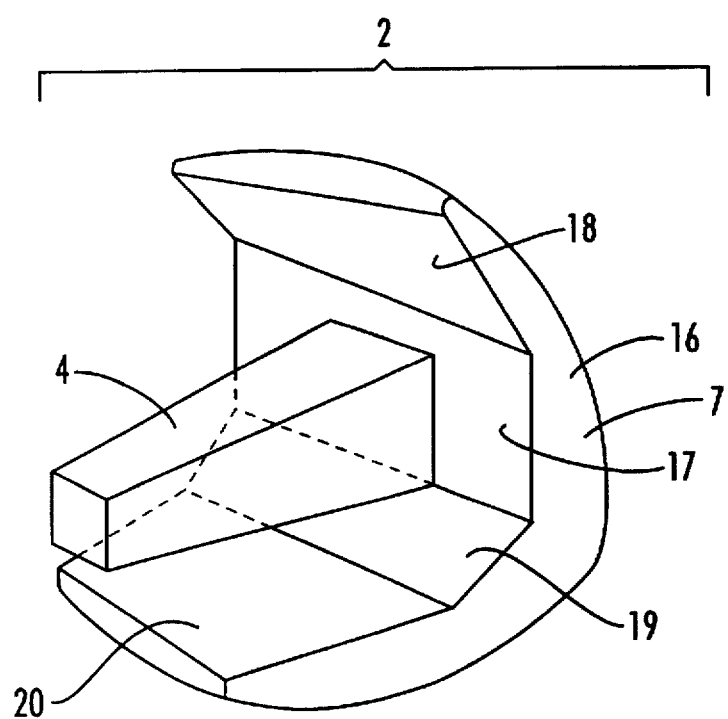
FIG. 5 is a front perspective view of the metatarsal component of FIG. 3.

In use, the stem 4 of the metatarsal component 2 is implanted into the distal end of the metatarsal bone and the remaining metatarsal cancellous bone exposed at the distal end is engaged by posterior surfaces of the head 7, i.e., a stem bearing surface 17, to which a posterior superior surface 18 and a posterior inferior surface 19 are inclined, and a posterior anterior horizontal surface 20 extending from the surface 19 of the head 7, best illustrated in FIG. 5. The convex bearing surface 16 of the head 7 extends dorsally and plantarly. i.e., over the stem 4 forming a retrograde concave aspect contacting the resected end of the metatarsal bone. The stem bearing surface 17 is at an angle of approximately 75 degrees to the axis 27 of the stem 4. Thus, as illustrated in FIG. 1, a plane 25 drawn parallel to the surface 17 is at an angle of 75 degrees with the axis 27, and at a neutral resting position in use of the joint, this plane is approximately perpendicular to the surface 26 of the ground and provides approximately 15 degrees of metatarsal declination. i.e., the angle that the axis 27 makes with the ground 26 which is the complement that the axis 27 makes with the plane 25.

Figure 4:
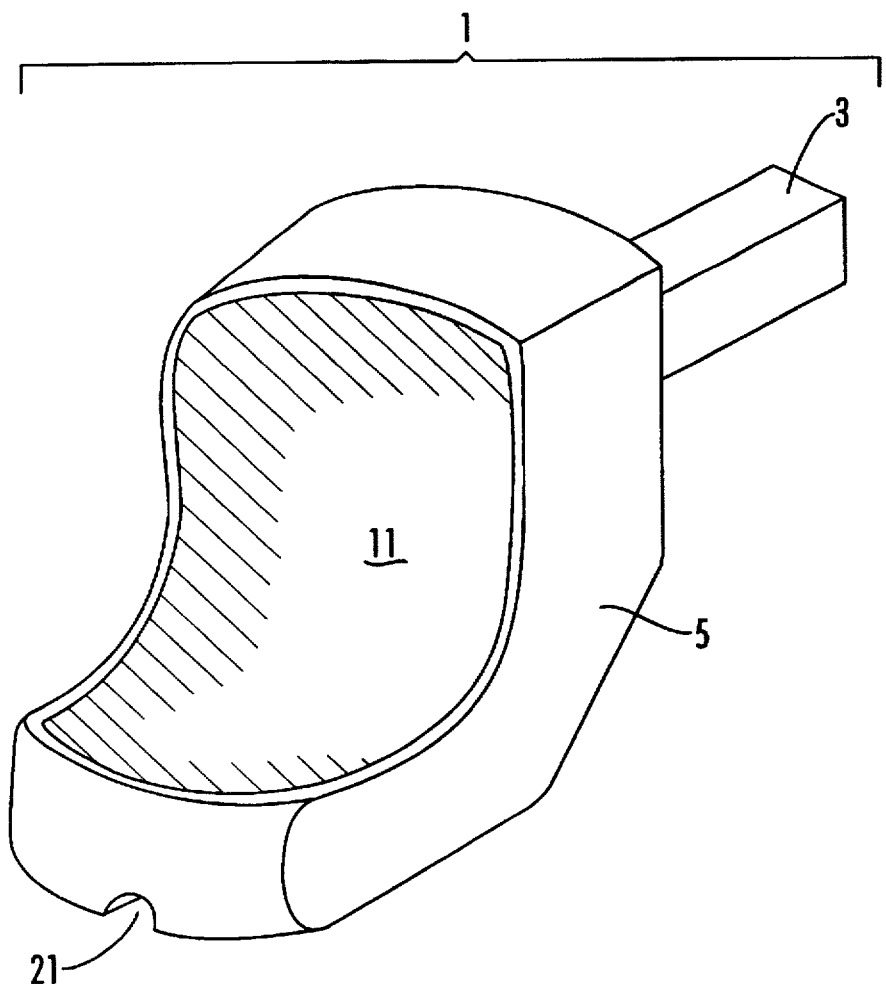
FIG. 4 is a front perspective view of the phalangeal component of FIG. 2.

As illustrated in FIGS. 2 and 4, the dual sesamoid support 5 in the base, i.e., the portion which engages the surface 26 in use, has an elongated flexor groove 21 for permitting passage of the flexor halucis brevis tendon of the person having the implant. This groove divides the base of the sesamoid support 5 into two portions which mimic or simulate the sesamoid bones by dispersing weight from the great toe joint above. Thus, the groove permits the placement, function and normal mechanical advantage of the flexor halucis longus. The dual artificial support member 5 consequently provides a stable surface for the metatarsal implant head 7 to bear the full weight of the body of the person within whom the joint has been implanted.

It may be noted, and it should be understood, that the prosthetic joint of the present invention provides a large surface area for the gliding insert 6 beneath the metatarsal head 7 and permits a full range of motion needed for normal gait since the plantar aspect of the metatarsal head is supported and this is where the greatest compressive forces are seen, and hence the greatest friction occurs. It also prevents uncontrolled dorsiflexion and drift of the hallux joint, a complication resulting from the surgical removal of the flexor brevis and the sesamoids. The gliding insert 6 also increases fluidity and minimizes entrapping healing tissue, debris, scar tissue, fat globules and hematomas.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

We claim:

1. A prosthetic joint replacement between a posterior metatarsal bone and an anterior phalangeal bone of a human toe comprising, a metatarsal component in the form of a metallic body member having a head including an anterior convex articulating surface and a posterior stem for implantation into an end of the metatarsal bone, said articulating surface defining a bearing surface, a phalangeal component having a metallic sesamoid support member and a plastic articular insert, said support member having a posterior concave surface and an anterior stem for implantation into an end of the phalangeal bone, a recess formed in at least portions of said concave surface including notches for receiving said insert, whereby said convex articulating surface of said head may articulate against said insert, and an elongated groove recessed into and extending along a plantar surface of said sesamoid support member in a posterior to anterior direction to define a passageway for the human flexor halucis longus tendon to extend therethrough.

2. A prosthetic joint replacement as recited in claim 1, wherein said sesamoid support member has at least a plantar portion disposed at the posterior of said insert, and said insert extends toward the posterior of said head so as to provide a large bearing surface beneath said head.

* * * * *